United States Patent [19]

Kumpe et al.

[11] Patent Number: 4,960,757
[45] Date of Patent: Oct. 2, 1990

[54] PASTEURIZED HUMAN FIBRINOGEN (HF), A PROCESS FOR ITS PREPARATION, AND ITS USE

[75] Inventors: Gerhardt Kumpe, Wetter; Wilfried Wormsbacher, Kirchhain; Norbert Heimburger, Marburg; Peter Fuhge, Lahntal-Caldern; Hans M. Preis, Marburg, all of Fed. Rep. of Germany

[73] Assignee: Behringwerke Aktiengesellschaft, Marburg, Fed. Rep. of Germany

[21] Appl. No.: 227,481

[22] Filed: Aug. 1, 1988

Related U.S. Application Data

[63] Continuation of Ser. No. 40,756, Apr. 16, 1987, abandoned, which is a continuation of Ser. No. 691,369, Jan. 14, 1985, abandoned, which is a continuation of Ser. No. 523,883, Aug. 17, 1983, abandoned.

[30] Foreign Application Priority Data

Aug. 19, 1982 [DE] Fed. Rep. of Germany ....... 3230849

[51] Int. Cl.$^5$ ................... A61K 37/02; A61K 35/16; C07K 15/06
[52] U.S. Cl. .......................... 514/21; 514/2; 514/802; 514/970; 514/8; 530/382
[58] Field of Search ................ 424/101, 154; 435/236; 514/802, 2, 21, 970; 530/382

[56] References Cited

U.S. PATENT DOCUMENTS 4,297,344 10/1981 Schwinn et al. .
4,327,086 4/1982 Fukushima et al. ................ 424/101
4,405,603 9/1983 Schwinn et al. .
4,440,679 4/1984 Fernandex .

FOREIGN PATENT DOCUMENTS 0035204 9/1981 European Pat. Off. .

OTHER PUBLICATIONS

Marguerie, "The Binding of Calcium to Fibrinogen", Biochimica et Biophysica Acta 494(1977) 172–181.
Altman et al., eds., *Biology Data Book*, pp. 1751–1753 2nd ed. vol. III.
Lawrie et al., "The Presence of a Catt Bridge . . . " Biochim et Biophys Acta 577 (1979) pp. 415–423.
Chem. Abstracts, vol. 86:91761p Lim, Jong Jir.

*Primary Examiner*—Jacqueline Stone
*Attorney, Agent, or Firm*—Finnegan, Henderson, Farabow, Garrett & Dunner

[57] ABSTRACT

A pasteurized human firbinogen which can be used therapeutically, and a process for its preparation are described.

11 Claims, No Drawings

PASTEURIZED HUMAN FIBRINOGEN (HF), A PROCESS FOR ITS PREPARATION, AND ITS USE

This application is a continuation of application Ser. No. 040,756, filed Apr. 16, 1987 which was a continuation of application Ser. No. 691,369, filed Jan. 14, 1985, which was a continuation of application Ser. No. 523,883, filed Aug. 17, 1983, all abandoned.

The invention relates to a pasteurized human fibrinogen (HF), a process for its preparation and its use in medicaments.

HF is a very important blood coagulation factor, which is at the end of the so-called clotting cascade: when the coagulation system is activated, for example after injuries, HF is converted by thrombin from its soluble form into fibrin, which is insoluble and which makes an essential contribution to hemostasis and the healing of wounds. HF is the coagulation factor which occurs in the plasma as the only effective substrate of all the other coagulation factors, and also in the highest concentration, namely between 250 and 400 mg %. Because of its importance for hemostasis and healing wounds, HF is used clinically, for example in consumptive reactions such as disseminated intravascular coagulation (DIC) in septicemias. In addition, fibrinogen is recently also used as a so-called "adhesive" instead of stitches or for sealing stitches, mainly in surgical operations and particularly on soft tissue organs, such as the liver and the spleen.

HF which has been obtained from the plasma of hepatitis B carriers involves the risk of transmitting hepatitis, since it is obtained from plasma fractions in which it occurs associated with other high-molecular and sparingly soluble proteins which are regarded as so-called hepatitis trap fractions. For the reasons mentioned, HF has hitherto only been used in the case of distinctly vital indications, because the risk of transmitting hepatitis cannot be excluded with absolute certainty. A further point contributing to this is that hitherto there has not been an absolutely reliable test for hepatitis B, to say nothing of non-A/non-B hepatitis.

The need for a hepatitis-proof HF, such as can be prepared, for example, by combining a fractionation process with a subsequent pasteurizing step, results from this situation. However, it is known to every expert in the field of blood coagulation, that plasma can be defibrinated by heating to 58° C. (3 minutes) because HF is one of the heat-labile proteins. Thus, a fibrinogen-free preparation is obtained on heating F VIII, as is described in German Patent No. 2,916,711 "Blood coagulation factors and a process for their preparation" (U.S. Pat. No. 4,297,344). The findings of European Patent No. 0,035,204, in which it is stated on pages 23/24 that HF can only be protected against inactivation by heat in a concentration of 0.05-0.4% by known stabilizers, such as carbohydrates, are also in agreement with this.

In view of these observations and findings, it was very surprising that it is possible, in accordance with the invention, to heat HF in concentrations of up to 7% for over 10 hours at 60° C. without the bulk of the HF being thereby precipitated, as described in European Patent No. 0,035,204.

In the process according to the invention, HF is dissolved, in a purity of 85% and in a concentration of 1 to 7%, in an aqueous solution of pH 6–8, containing at least 1 g atom of calcium per mole of HF, and carbohydrates (monosaccharides or oligosaccharides or sugar alcohols) or a mixture of such carbohydrates and aminoacids, preferably sucrose and glycine, are added as stabilizers. The calcium, the carbohydrates and the aminoacids are added in a concentration adequate for the stabilization, and are advantageously added to the HF solution in the sequence $Ca^{2+}$, carbohydrates, for example sucrose, and an aminoacid, for example glycine. Solutions of this type can be kept, and pasteurized, for several hours at temperatures up to 60° C.

The invention relates, therefore, to a pasteurization process for HF in aqueous solution, which, in addition to customary stabilizers, is carried out in the presence of Ca ions in a concentration of 1 to 37,800 g atoms, preferably 1 to 10 g atoms per mole of human fibrinogen.

Amongst the customary stabilizers, sucrose, in a concentration of 35 to 60 g/100 ml of solution, and glycine, in a concentration of 0.5 to 3 moles/liter, are preferred.

This solution is heated in a manner which is customary per se. It is advantageously heated at at least 60° C., but not more than 100° C., for at least 10 hours, but not more than 24 hours.

The fibrin polymers which can be present in the purified HF solutions and whose concentration can still increase during the heating at 60° C., are removed after heating, if appropriate by precipitation, preferably using 0.25 to 1.5 mole/liter of glycine, and the HF is obtained from the supernatant liquid, and at the same time separated from the stabilizers, by increasing the concentration of the precipitant, for example the glycine concentration, to at least 2.2 moles/liter (2.0–2.7 moles/liter).

A very clean, natural, polymer-free, pasteurized HF which has good solubility properties and can be used in a very broad therapeutic field, preferably as an infusion solution containing approx. 2% (w/v) of HF or as a tissue adhesive containing approx. 10% (w/v) of HF, is obtained by these process stages. Agents of this type also form a subject of the invention.

The invention is illustrated in greater detail in the Example below:

EXAMPLE

Starting material 500 g of a fibrinogen-containing residue from precipitation by 2.7 moles/liter of glycine, such as is obtained in the preparation of factor VIII concentrate HS (German Patent No. 2,916,711), were dissolved in 1,250 ml of 0.15 mole/liter NaCl solution by warming to 37° C. and stirring, and the pH was adjusted to 7.5 with 2N NaOH. After the material had dissolved, 1,700 ml of a 6% strength solution of fibrinogen were obtained.

Stabilization and pasteurization (A) 5 mmoles/liter of $CaCl_2 \cdot 2H_2O$ (1,250 mg) were added to 1,700 ml of fibrinogen solution from 1., and the mixture was stirred until solution took place. When the $CaCl_2$ added had dissolved completely, 60% strength (w/v) sucrose (1,700 g) were added, while stirring and warming.

When the sucrose had dissolved completely, 1 mole/liter of glycine (127.5 g) was added. When the glycine had dissolved completely, the pH value was adjusted to 7.5 with 2N NaOH. This gave an opalescent, very viscous solution, which was then incubated for 10 hours at 60° C. on a waterbath.

In order to remove fibrin polymers (3) and to isolate the fibrinogen (4), the fibrinogen solution which had been heated was treated further as follows:

After heat treatment at 20° C., 2.9 liters of stabilized, heated fibrinogen solution were diluted in a ratio of 1:4 with 8.7 liters of buffer (0.06 mole/liter NaCl—0.02 mole/liter tri Na citrate), to give 11.6 liters of heated, dilute fibrinogen solution, which was fractionally precipitated with glycine.

(B) Process A above can also be carried out with the desired stabilization effect using a comparatively high concentration of Ca ions, for example with 1.8 moles/liter $CaCl_2 \cdot 2H_2O$ (449.8 g).

Removal of the high-molecular constituents, principally the fibrin polymers 86.25 g of glycine/liter (=1.15 moles/liter) were added at 37° C. to the fibrinogen solution which had been heated and then diluted. After the glycine had dissolved, the mixture was cooled to 20° C. and the resulting precipitation was removed by means of a Stock centrifuge.

Isolation of the fibrinogen from the stabilizer medium

The supernatant liquid from 3., containing 1.15 moles/liter of glycine, was warmed again to 37° C., further glycine was added to it to give a final concentration of 2.2 moles/liter, and the mixture was stirred (30 minutes) until the glycine had dissolved completely.

The precipitate was cooled to 20° C. and removed in a Stock centrifuge.

For use as human fibrinogen for intravenous infusion, the fibrinogen residue was dissolved to form a 2% strength solution in 2,500 ml of 0.01 mole/liter tri Na citrate—0.15 mole/liter NaCal, dialyzed against the same buffer, clarified and filtered under sterile conditions and bottled and Lyophilized in volumes of 60 ml (1 g of HF).

In order to prepare "fibrin adhesive", a 4% strength fibrinogen residue which had been obtained by the same procedure was dissolved in 1,250 ml of the following salt solution: 0.05 mole/liter NaCl; 0.005 mole/liter tri Na citrate; 0.01 mole/liter $NaHCO_3$; and 0.33% L-arginine monohydrochloride, pH 7.5; and the mixture was dialyzed (dissolved buffer) and then ultracentrifuged: 1 hour at 35,000 g. After clarification and filtration under sterile conditions, the product is lyophilized in 4 ml portions.

After reconstitution, and in combination with F XIII and thrombin, this product is suitable for producing adhesion in soft tissues and for sealing vessel sutures.

We claim:

1. A process for the pasteurization of human fibrinogen comprising the step of heating, at a temperature between 60° to 100° C. for 10 to 24 hours, an aqueous solution of human fibrinogen in the presence of (a) a thermally stabilizing amount of a carbohydrate selected from the group consisting of monosaccharide, oligosaccharide, sugar alcohol, and mixtures thereof, (b) an amino acid or mixture of amino acids, and (c) calcium ions in a concentration of 1 to 37,800 g atoms/mole of human fibrinogen.

2. The process as claimed in claim 1, wherein the concentration of calcium ions is 1 to 10 g atoms/mole of human fibrinogen.

3. Pasteurized human fibrinogen produced in accordance with claim 1.

4. A human intravenous infusion solution comprising pasteurized human fibrinogen as claimed in claim 3.

5. A process for producing adhesion between living human tissues comprising application of pasteurized human fibrinogen as claimed in claim 3.

6. The process as claimed in claim 1, wherein said aqueous solution of human fibrinogen has a concentration of 1 to 7% (w/v).

7. In a process for the pasteurization of human fibrinogen by heating an aqueous solution of human fibrinogen in the presence of (a) a thermally stabilizing amount of a carbohydrate selected from the group consisting of monosaccharide, oligosaccharide, sugar alcohol, and mixtures thereof and (b) a thermally stabilizing amount of an amino acid or a mixture of amino acids, the improvement comprising heating the aqueous solution of human fibrinogen between 10 to 24 hours at a temperature of between 60° to 100° C. in the additional presence of calcium ions in a concentration of 1 to 37,800 g atoms per mole of human fibrinogen.

8. The process as claimed in claim 7 wherein the improvement further comprises adding the calcium ions, carbohydrates, and amino acids in the following sequence: calcium ions, carbohydrates, and amino acids.

9. The process as claimed in claim 8, wherein the improvement further comprises pasteurizing an aqueous solution of human fibrinogen having a concentration of 1 to 7% (w/v).

10. The process as claimed in claim 8, wherein the concentration of calcium ions is 1 to 10 g atoms/mole of human fibrinogen.

11. The process as claimed in claim 7 wherein the improvement further comprises heating the aqueous solution of human fibrinogen in the presence of
   (a) a carbohydrate consisting of sucrose in a concentration of 35 to 60 g/100 ml of solution,
   (b) an amino acid consisting of glycine in a concentration of 0.50 to 3 moles/liter, and
   (c) calcium ions in concentration of 1 to 10 g atoms/mole of human fibrinogen.

* * * * *